United States Patent [19]

Sowman et al.

[11] Patent Number: 4,743,511
[45] Date of Patent: May 10, 1988

[54] GRADED REFRACTORY CERMET ARTICLE

[75] Inventors: Harold G. Sowman, Stillwater; David R. Kaar, Minneapolis, both of Minn.

[73] Assignee: Minnesota Mining and Manufacturing Company, St. Paul, Minn.

[21] Appl. No.: 99,081

[22] Filed: Sep. 21, 1987

Related U.S. Application Data

[62] Division of Ser. No. 809,067, Dec. 13, 1985, Pat. No. 4,713,300.

[51] Int. Cl.$^4$ .............................................. B22F 3/00
[52] U.S. Cl. ..................................... 428/547; 419/10; 419/19; 419/24; 419/29; 419/53; 419/54; 419/57; 419/58; 428/539.5; 428/610; 428/545
[58] Field of Search ............ 428/545, 547, 610, 539.5; 419/10, 19, 24, 29, 53, 54, 57, 58

[56] References Cited

U.S. PATENT DOCUMENTS

| | | | |
|---|---|---|---|
| 3,148,981 | 9/1964 | Ryshkewitch | 428/547 |
| 3,321,285 | 5/1967 | Sowman | 29/182.5 |
| 3,460,971 | 8/1969 | Boals et al. | 117/71 |
| 3,560,408 | 2/1971 | Kiehl et al. | 252/463 |
| 3,579,390 | 5/1971 | Paine | 428/547 |
| 3,773,549 | 11/1973 | Elbert et al. | 117/129 |
| 3,953,177 | 4/1976 | Sedlatschek et al. | 428/539.5 |
| 3,975,165 | 8/1976 | Elbert et al. | 428/553 |
| 4,147,911 | 4/1979 | Nichitani | 219/10.55 |
| 4,234,338 | 11/1980 | Morgan et al. | 75/235 |
| 4,327,131 | 4/1982 | Branovich et al. | 427/229 |
| 4,397,963 | 8/1983 | Morgan | 501/127 |
| 4,404,262 | 9/1983 | Watmough | 428/539.5 |
| 4,525,387 | 6/1985 | Ebata et al. | 427/190 |

Primary Examiner—Stephen J. Lechert, Jr.
Attorney, Agent, or Firm—Donald M. Sell; James A. Smith; Lorraine R. Sherman

[57] ABSTRACT

This invention provides a shaped, graded, cermet article comprising at least one continuous ceramic phase and at least one discontinuous metal phase, the ratio of ceramic/metal being controlled and varied over the thickness of the article. The ceramic phase preferably is microcrystalline.

11 Claims, 2 Drawing Sheets

GRADED REFRACTORY CERMET ARTICLE

This is a division of application Ser. No. 06/809,067 filed Dec. 13, 1985, now U.S. Pat. No. 4,713,300.

TECHNICAL FIELD

This invention relates to shaped cermet articles, and a process therefor, the articles comprising a continuous ceramic phase and a discontinuous metal phase. The cermet articles are in fibrous and other forms.

BACKGROUND OF THE INVENTION

Oxide ceramics are strong and resistant to both creep and oxidation at high temperatures. However, for many applications, they are brittle and susceptible to thermal shock failure. On the other hand, metals, which are ductile and less prone to thermal shock failure are susceptible to destructive oxidation at high temperatures. A combination of the desirable qualities of ceramics with those of metals has led to materials called cermets, from combining and contracting the words ceramic and metal.

Technology in ceramic-metal systems can be divided into two general areas. One area is classical cermet technology where metals are incorporated with ceramics in the form of powder, grains or granules, or by molten infiltration or by powder metallurgy techniques followed by suitable heat treatment.

A second area is the in-situ reduction of metal oxides or metal salts in and on the ceramic to form the metal. Widespread application for this area has been in the art of supported catalysts and catalysis.

Generally the term cermet is used to describe a ceramic matrix material having metallic particles dispersed in the ceramic body. The term is also used to describe the reverse, that is, a metal matrix having dispersed therein refractory or ceramic materials which impart ceramic-like characteristics to the cermet. Cermets are known in the art and have been described in the patent literature.

The background art has taught a mixture of metal fibers in ceramics which can be a physical mixture or formed by the reduction of a mixture of ceramic and metal oxide in a reducing atmosphere. Representative patents teaching such mixtures include U.S. Pat. Nos. 4,397,963; 4,147,911; 3,560,408; and 3,321,285.

The background art also taught a ceramic coated with a metal or the hydrogen reduction of a ceramic coated with metal oxide, including fibers, to give refractories having a variety of uses as in, for example, U.S. Pat. Nos. 4,525,387; 4,327,131; 4,234,338; and 3,460,971.

SUMMARY OF THE INVENTION

Briefly, this invention provides a shaped, graded, cermet article comprising at least one continuous ceramic phase and at least one discontinuous metal phase, the ratio of ceramic/metal being controlled and varied over the thickness of the article. The ceramic phase preferably is microcrystalline which is the result of firing at temperatures above approximately 800° C.

The opaque, shaped cermet of the invention, which can be fibrous, has a unique new graded microstructure comprising a metal phase intimately mixed on a submicron scale with a microcrystalline oxide ceramic matrix, the metal phase being present in greatest quantity on the exterior of the article and diminishing in quantity towards the interior of the article. The cermet can have a textured surface comprising metal nodules, generally submicron in size. The composition of the ceramic/metal article may be controlled and varied over the depth of the article by regulation of components in a heated reducing atmosphere which preferably is hydrogen gas.

In another aspect a process for providing cermet articles having desired high performance physical properties is disclosed. These properties are maximized by controlled firing of the cermet precursor to develop the desired ceramic, then firing in a reducing atmosphere, preferably hydrogen, to develop the desired metallic phases and produce resultant articles or where under proper conditions both ceramic and metallic phases can be developed contemporaneously with a single firing. The cermet articles of the invention can be reoxidized to provide an active oxide surface of controlled composition. The reoxidized cermet articles can have a cermet/oxide composition which is graded.

Preferably, the shaped cermet article can be a fiber which has a graded ceramic/metal content, the metal component decreasing from the periphery towards the center of the fiber with a predominant amount of the metal on the surface, the metal being in the form of discrete, preferably spheroidal metal particles separated from each other so as to provide an electrically nonconductive cermet. These fibers are black in color or metallic-appearing, mechanically strong and, when nickel, iron, and cobalt are present, can be attracted to a magnet. Scanning Electron Microscopy (SEM) shows the presence of a large number of nodules which can be protruding from the surface of the fiber. These were identified as metal by X-ray diffraction analysis. The metal nodules vary in diameter from hundreds to a few thousand angstroms, with a typical diameter of 0.1 micrometer (1000 Å). Magnetic measurements (Curie temperature and saturation moment) confirm that the metal is present in the metallic state and indicate that reduction can be over 95% complete. Because the nodules are not in contact with each other, the fibers are found to be electrically nonconducting.

The articles can be refractories, such as fibers, powders, films, flakes, microspheres, bubbles, granules, particles and the like and are useful as reinforcing structures, composites, catalysts, and abrasives materials. The materials of this invention, and preferably those in fiber form, are useful for reinforcement of and use in metal, ceramic, and polymer matrix composites. In particulate form this material is useful as a raw material to form cermet composites, and for oxide dispersion strengthening of metals. In granular form this material is useful as an abrasive. In general, this material is useful as a catalyst in hydrogenation, dehydrogenation, oxidation and other reactions, as a support for other catalysts including those of biological origin, as an active surface to enhance bonding to other metals, polymers, or to itself, and as a microwave absorber.

Cermets of this invention are unique in that they require only modest firing temperatures (e.g., 800° to 1000° C.) in contrast to the teachings in ceramic and cermet art in general.

The refractory non-fused cermet articles of the invention are relatively inexpensive and have desirable physical properties such as high strength, high thermal emissivity, high modulus of elasticity, chemical resistance, and retention of such properties after exposure to high temperatures.

In this application,

"graded cermet article" means an article in which the ratio of ceramic/metal is controlled and varied over the thickness of the article; such a cermet article may exhibit a graded or gradual change from less than 100 weight percent metal content on the outer surfaces to 0 weight percent metal content on the innermost portions, preferably in the range of 10 to 95 weight percent metal content on the outer surfaces (those surfaces in contact with the reducing atmosphere) to approaching 0 weight percent metal content in the innermost portions of the article.

"non-fused ceramic" means any inorganic nonmetallic material (includes metal oxides) which requires the application of high temperatures at some stage in its manufacture but is not derived from a melt of the oxide composition;

"transition metal oxide spinel" or "transition metal spinel" means a ceramic having the general formula $M^1(M^2)_2O_4$ where $M^1$ is a divalent cation of a transition metal such as cobalt, iron, and nickel, or combinations thereof, and $M^2$ is typically a trivalent metal cation, usually aluminum but sometimes iron (for example ferrites) or chromium, or combinations thereof. The resultant spinel has typically a cubic, or nearly cubic structure. When $M^2$ is aluminum, the anion $(M^2)_2O_4^{-2}$ is referred to as the aluminate anion and the spinel arising therefrom is referred to as an aluminate spinel;

"matrix" means the predominant continuous phase;

"phase" means a component that exists as a distinct and separate portion or portions, distributed or continuous, throughout a heterogeneous system;

"crystalline phase" means a phase which gives a discernible X-ray powder diffraction pattern. A microcrystalline material is one made up of small crystallites. Many microcrystalline ceramics are transparent or translucent;

"microcrystalline" means a crystalline phase having a crystallite size of about 50 angstroms (A) or less up to 1000 A ($5 \times 10^{-9}$ to $1 \times 10^{-7}$ m), and sometimes larger but always less than 10,000 A ($1 \times 10^{-6}$ m). Such a microcrystalline structure may be transparent to visible light, providing the material itself is not opaque and does not contain large pores or opaque fillers and the like.

"microstructure" means the internal structure, that is, the structure of grain boundaries, the size, shape, and orientation of grains, as well as the phases and their morphology. Microstructural details require magnification to be observed;

"refractory" means a material maintains its integrity or usefulness even at temperatures in the range of 820° to 1400° C.;

"green" refers to ceramic articles which are unfired, that is, not in their final ceramic form;

"dehydrative gelling" or "evaporative gelling" mean that sufficient water and volatile material are removed from the shaped green article so that the form or shape of the article is sufficiently rigid to permit handling or processing without significant loss or distortion of the desired articles' form or shape;

"amorphous" means a material having a diffuse X-ray diffraction pattern without definite lines to indicate the presence of a crystalline component;

"transparent" means that the material, when viewed under an optical microscope, (e.g., with a stereoscopic microscope at 50× and under oblique or transmitted light,) has the property of transmitting rays of visible light so that images of an article viewed through the material have sharp edges;

"translucent" means that the material, when similarly viewed, has the property of transmitting visible light to some degree so that images have unclear or blurred edges;

"opaque" means that the material, when similarly viewed, has the property of being impervious to visible light;

(Sometimes because of vagaries in firing, an article may be a mixture of these above various types (i.e., transparent, translucent, and opaque), though generally, one type will be present in a predominant amount, indicative of the true nature of the mixture, the other types present in minor amounts having their particular appearance due to incomplete firing at the desired temperature or due to overheating because of hot spots in the furnace.)

"sol" means a colloidal dispersion of a finely divided solid phase in a liquid medium;

"fiberization" means the process of forming fibers from a viscous liquid precursor, and "high performance properties" means physical properties such as high strength, high thermal emissivity, high modulus of elasticity, chemical resistance, electrical non-conductivity and retention of such properties after exposure to high temperatures.

DETAILED DESCRIPTION

The present invention provides a novel, graded, cermet article comprising a first, major, electrically non-conductive, continuous phase containing a transition metal oxide aluminate spinel, especially $NiAl_2O_4$, and solid solutions with it, and/or alumina phases such as alpha, gamma, or eta, and the like, or mixtures of non-spinel oxides such as alumina, boria, silica, zirconia, magnesia, beryllia, titania, or phosphorus oxide, or combinations thereof.

Preferably, the cermet article of the invention comprises a cermet fiber or other shaped form having a first continuous, preferably microcrystalline, transition metal oxide spinel or an alumina-boria-silica ceramic phase as the major constituent (i.e., preferably 50 weight percent or more) and a second discontinuous metal phase, the ratio of ceramic/metal being controlled and varied over the thickness of the article.

These articles are made under non-fusing conditions, i.e., without melting or fusing the entire constituent oxide composition, and at temperatures below those commonly used under sintering conditions for these same compositions. When an excess of constituent oxides is present beyond those necessary for the stoichiometric spinel composition, there is then provided the spinel composition plus an additional oxide phase. Transition metal oxide spinels useful in the present invention are disclosed in assignee's copending patent application U.S. Ser. No. 097,369, filed the same date as this application.

The second discontinuous, graded, metal phase, preferably, is selected from the transition metals Ni, Fe, Co, Cu, and Pb, or their combinations.

Figure 1:
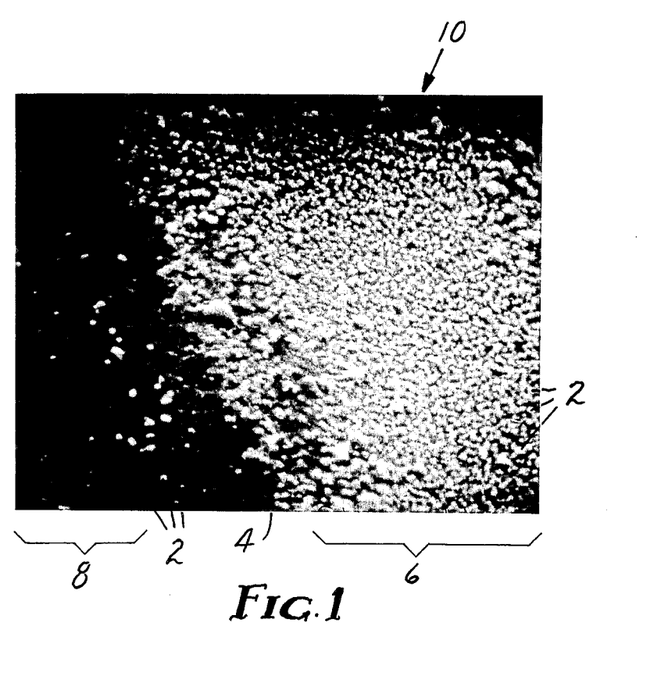
FIG. 1 shows a photomicrograph of a portion of a broken fiber of a graded cermet article of the present invention, enlarged 15,000 times.
Figure 2:
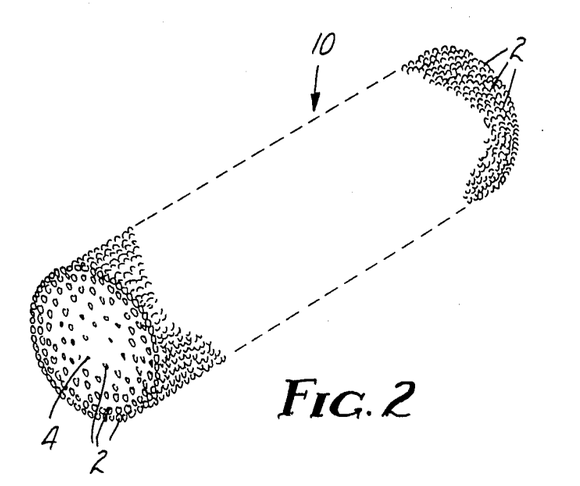
FIG. 2 is an enlarged perspective view of the graded cermet article of FIG. 1.
Figure 3:
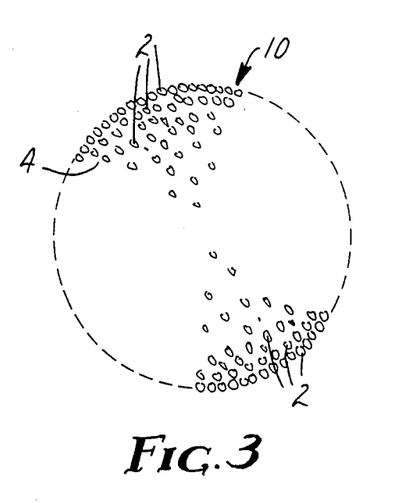
FIG. 3 is an enlarged cross-sectional view of the graded cermet article of FIG. 2.

Referring to FIGS. 1, 2, and 3, one embodiment of the cermet article of the invention is shown. Individual fiber 10 is shown comprising ceramic matrix 4 and embedded therein nodules of metal 2. Nodules of metal 2 protrude from the surface of fiber 10 as well as being present throughout fiber 10 to provide a graded ceramic/metal composition. The density of nodules of metal 2 is greatest in the surface portions 6 of fiber 10 and decreases towards the interior portions 8 of fiber 10.

The refractory cermet articles of this invention have compositions comprising 58 to 96 weight percent of a ceramic phase (for example, 21 to 95 weight % can be alumina, 0 to 25.5 weight % boria, and 0 to 65 weight % silica), and 4 to 42 weight percent metal content, preferably 10 to 40 weight percent, most preferably 20 to 30 weight percent, (for example, wherein the metals are Cr, Cu, Co, Fe, Ni, Pb, Mo, W and combinations thereof).

Preferred refractory cermets of this invention have compositions within the range by weight of 62 to 87% of alumina, 0 to 25.5% of boria, and 0 to 35% of silica, and 10 to 24% metallic phases, wherein the metals are as stated above.

The refractories may also contain amorphous species and have, for example, an overall composition range by weight of 21 to 79% alumina, 0 to 50% silica, 0 to 19% boria, 0–42 % nickel oxide, 0–28% metal content or such metal combinations wherein the metals comprise chromium, cobalt, copper, iron, lead, and nickel.

In another aspect, this invention provides a non-melt process for preparing cermet articles comprising:
  (1) formulation of a stable concentrated aqueous composition of at least one of soluble metal salts, carboxylates, and oxide sols with organic fugitives as needed;
  (2) formation of an engineered shape from the concentrate or dilute sol - e.g., spinning of fibers, spray drying of powders, or gelling to form granules or microspheres;
  (3) conversion of the engineered shape to the final cermet material by the controlled application of heat in a controlled environment, involving drying and dehydration, decomposition, densification, and reduction (preferably in a hydrogen atmosphere) to develop the desired graded and unique microstructure leading to the useful properties of the final material.

In general, as the firing temperature increases the degree of crystallinity increases. Surprisingly, in the presence of nickel, at about 820° C. the nickel aluminate spinel forms. Mechanical strength of the fired fibers generally increases with firing temperature to an optimum level and then decreases thereafter. When fired above the optimum firing temperature the fibers become less transparent. After reduction, preferably in a flowing, dry hydrogen atmosphere at a temperature in the range of 800° to 1000° C., preferably 800° to 900° C., at ambient pressures, the fibers become black or have a metallic appearance and contain discrete metallic particles.

Other useful reducing atmospheres include a hydrogen/argon mixture, carbon monoxide, hydrogen/helium, or hydrogen mixed with any inert carrier gas. A particularly useful mixture is 5 weight percent hydrogen and 95 weight percent argon.

The temperature of the furnace with the sample therein is normally raised over a period of about 1 hour to 800° to 1000° C. and can be maintained at elevated temperature for a period of several minutes to several hours depending on the size and configuration of the cermet and the gradation of the metal phase desired. Higher temperatures and longer times will increase the metal concentrations toward the exterior of the article.

Compositions of this invention are preferably based on an alumina transition metal spinel phase ($M^1Al_2O_4$, wherein $M^1$ is as defined above) with optional boria, silica, and other metal oxide additions in another phase. Excess transition metal oxides cannot be generally tolerated while excess $Al_2O_3$ is acceptable. Thus there is an upper limit on the amount of spinel-forming oxide which can be accommodated. This limit is a function of the amount of $Al_2O_3$ in a given composition; for example when $M^1$ is Ni, the optimum maximum amount of NiO which can be accommodated is that which produces stoichiometric $NiAl_2O_4$. For a ceramic composition of a cermet having a mole ratio 3 $Al_2O_3.1B_2O_3.2SiO_2$, approximately 24% by weight of the total composition can be NiO; however, a particularly useful range is 15 to 30 weight percent NiO. The maximum addition of NiO produces the maximum amount of spinel and the resultant properties associated with the spinel. Correspondingly, less NiO can be used to produce a lower value of the specific property sought, e.g., modulus, density, and the like. When $Fe_2O_3$ is added to the composition with NiO, the spinel formed is $(NiFe)(FeAl)_2O_4$, because iron is capable of partially substituting for either the $M^1$ or $M^2$ component in the spinel structure. Thus the total transition metal oxides which can be incorporated in the spinel phase is up to 40% by weight, preferably 2 to 40 weight percent, most preferably 10 to 24 weight percent.

Refractory articles of this invention are solid, shaped, fired, and non-vitreous, i.e. are made by a non-melt process comprising the steps of providing an aqueous liquid mixture containing transition and other metal compounds such as soluble salts, oxides, sols, or dispersible colloids, or mixtures thereof, concentrating the mixture to a viscous fluid, shaping the viscous concentrate into a desired form, for example, a fiber form as is taught in U.S. Pat. No. 4,047,965, and dehydratively or evaporatively gelling the concentrate which results in a "green" (i.e. unfired) or non-refractory amorphous article. In making continuous fibers, the viscous concentrate can be extruded through a plurality of orifices. By continuous is meant fibers having an aspect ratio of 1000 to 1 or greater.

Alternatively, more dilute or unconcentrated precursors may be formed into microspheres as taught in U.S. Pat. Nos. 3,795,524 and 4,166,147, or made into bubbles, granules, flakes or a coating on a substrate. Heating and firing the shaped green article removes water, decomposes and volatilizes organic constituents (fugitives), and converts the resultant form into a refractory article. All the water in the shaped article need not be removed. Thus, gelling can result from partial dehydration. Also, gelling can be accomplished by chemical means. Shaped articles in their green form are generally transparent to visible light and clear (or perhaps slightly hazy) under an optical microscope, provided they do not contain opacifying materials.

Precursors to the cermet composition can comprise salts and inorganic oxides which are used in preparing aqueous mixtures of solutions, sols, or solutions and sols for making the cermets of this invention and are well known in the art and are commercially available from numerous sources. Alternatively, the precursor can comprise non-aqueous systems such as metal alkoxides or mixtures of aqueous and non-aqueous systems. Specific sources are indicated in the appropriate examples below.

Generally, the use of salts having anions which are decomposed thermally in a controlled manner is preferable in the practice of this invention. Simple organic anions (e.g., acetate, formate) are preferred over inorganic anions (e.g., sulfate, nitrate). However, excessive organic anions may cause firing problems. Therefore, it is preferable that part of the mixture composition be introduced as a sol, since this helps to minimize the amount of decomposable fugitive. Using a sol of dispersed metal oxide colloids also imparts strength to the green material.

Many divalent transition metals will, under the proper firing conditions, react with suitable aluminum compounds to form spinels. Usually these conditions require 1000° C. or higher. In the teachings of this invention however, surprisingly, nickel aluminate spinel is formed at about 820° C., appreciably lower than that taught in the background art. A preferred temperature range is 820° C. to 1000° C. to fully develop the desired properties of the refractory article.

Also surprising, we have found that not only do nickel aluminate spinels form ceadily, but the presence of nickel induces and promotes the formation of other transition metal aluminate spinels, such as nickel-iron aluminate spinels, whereas for example when iron alone is added to alumina, iron tends to form a mixed oxide with alumina rather than form a spinel.

Concentration of the mixture for article formation can be carried out by techniques known in the art (see U.S. Pat. No. 3,795,524 and related art cited therein). For example, the mixture can be concentrated in a rotary evaporator flask under water-aspirator vacuum, the vacuum adjusted to prevent or minimize frothing or loss of the sol. Sufficient concentration, when fibers are prepared, will be obtained when the equivalent solids content of a calcined sample is generally 25 to 55 weight percent, and the viscosity (Brookfield at ambient temperature) of the concentrate is in the range of 15 Pa.S to 1,000 Pa.S, preferably 25 to 500 Pa.S. (Pa.S=1,000 centipoise or cps).

The viscous concentrate can contain various other water-soluble transition metal compounds which will impart additional desired properties to the refractory articles upon being converted or oxidized to the corresponding alumina spinel. Chromium formate or acetate will impart a green color to the greenware whereas chromium trioxide will impact an orange color; cobalt acetate or nitrate will impact a blue or lavender color; iron nitrate will impart a gold or brown color; and nickel acetate or nitrate will impart a blue green to gold color. In general, any suitable water-soluble transition metal compound such as the soluble nitrates, formates, acetates, citrates, lactates, tartrates, oxalates and the like may be used, provided they do not induce any precipitate formation when introduced into the dilute solution. Particularly in the preparation of fibers, on concentration of the dilute solution, care must be taken not to form a visible precipitate as the solubility limits of the constituent salts may be exceeded; however, as the solution is concentrated, the viscosity of the concentrate will increase and thus stabilize the concentrate.

Viscous concentrates are relatively stable but low temperature storage or refrigeration may be preferred if the concentrate is not to be used shortly after preparation, e.g., within one day.

Organic fugitives such as corn syrup or polyvinylpyrrolidone may be added to promote fiberization (via extrusion). Acids may be required in such solutions to stabilize them against crystallization.

Refractory articles can be prepared by using the shaping and dehydrative gelling techniques and equipment of the prior art (e.g., see U.S. Pat. Nos. 3,329,745, 3,331,783, 3,331,785, 3,340,567, and 3,380,783). This type of dehydrative gelling can be considered in a sense as a solvent extraction. Chemical gelation is also useful. Further details on the shaping of articles from the viscous concentrate will be omitted here in the interest of brevity since such shaping procedures are well known and referenced in the text "Modern Composite Materials" (Broutman and Krock, ed., Chapter 8, Addison-Wesley Pub. Co., Reading, MA, 1967).

After forming the desired shape (e.g. fiber, bead, flake, etc.) it is later necessary to heat and fire the greenware to remove all fugitives and to convert the greenware to refractory articles of this invention.

Shaping and firing to provide refractory articles of this invention can be accomplished as disclosed in U.S. Pat. No. 4,125,406 wherein it is taught that there is extruded in air a viscous concentrate of a mixture of solutions, sols, or sols and solutions and then drying and firing the resulting "green" forms at temperatures in the range of 500° to 1500° C. to give uniformly shaped, strong, flexible, smooth, glossy refractory materials. They can be made in an amorphous form by heating, for example, to a temperature in the range of of about 500° C. to less than 820° C. Such amorphous articles can be further heated to higher temperatures to densify, strengthen, and convert to a homogeneous mixture of amorphous and crystalline spinel phases or into an all crystalline spinel form with retention of desired shape, integrity, and transparency.

The firing step volatilizes the balance of water and anion components, decomposes and volatilizes organic material, and removes carbon to leave refractory articles. This firing step also causes some shrinking; however, the shape of the article during firing remains intact.

In firing the green articles of this invention, ignition of combustible and organic fugitive materials should be avoided since such ignition may cause a rapid rise in temperature or a catastrophic evolution of volatiles, resulting in the formation of opaque, fragile materials. Ignition may be avoided, for example, by starting out at a low temperature, such as room temperature, and elevating the temperature at a controlled rate to some intermediate temperature which is maintained for a certain length of time before the ultimate firing temperature is achieved. If the greenware is not to be fired completely in one operation or not to be fired immediately or soon after its formation, it may be desirable or necessary for storage in a relatively dry or protective atmosphere to prevent the greenware from picking up moisture or contaminants, and deteriorating or sticking together.

Rather than firing the greenware to remove water and organic material, greenware can be heated in a pressure vessel in an inert atmosphere (e.g. nitrogen, helium, argon) at 300° to 500° C. to form porous refractories. They can then be fired in air to remove residual fugitives such as carbon, at 500° C. Increasing the temperature up to about 820° C. or somewhat higher, e.g., 900° C., converts the porous refractories into a spinel essentially free of carbon.

The refractory material or product of this invention is generally useful where high temperature stability or refractoriness is desired or required, for example, 820° to 1400° C., preferably 1000° to 1400° C., depending upon the particular refractory used and the length of service at such high temperatures. It should be noted that above such temperatures, i.e., above 1400° C., microstructure changes such as crystal growth occurs, and the refractory products of this invention generally will begin to lose strength and flexibility, coincident with the extent and growth of the crystallites into larger forms. The resultant changes are deleterious to the mechanical properties, especially strength and flexibility.

Cermet articles of the present invention can have varied properties. They are generally opaque and black or of a metallic luster, depending upon the composition and the temperature at which they are fired. Also, firing the articles at temperatures somewhat above 800° C. tends to convert the composition to a predominantly microcrystalline form. The resulting microcrystallites of the ceramic matrix are estimated to be between 50–1000 A.

X-ray data reported are those obtained at room temperature with a Picker X-ray (Picker Corp., Cleveland, Ohio) diffraction instrument, 816 A, at 40 kv, 30 ma, using a powder diffraction camera (Debye-Sherrer) with an effective film diameter of 14.32 cm. Typically, the samples were powdered samples exposed 0.5 hour to copper K alpha radiation wavelength 1.5405 Angstroms, one-half of the film in the camera being filtered through a nickel filter. Where crystallite sizes are given in Angstroms (A), they are estimated average sizes, based on x-ray powder diffraction line broadening.

Transparency of the ceramic precursor articles (e.g., fibers, beads and the like) is an indication of uniformity of quality, absence of large pores, smooth surface characteristics, and for the fired articles, small crystallite sizes.

Cermets of this invention have been found to be generally non-porous which is consistent with increased strength. This lack of porosity has been observed by surface area measurement and optical microscopy. Surface areas measurements are determined by a nitrogen absorption technique using a Quantasorb TM, model SW-6, surface area measuring instrument (commercially available from Quantachrome Corp., Syosset, N.Y.).

As noted above, incorporation of transition metals in the ceramic fiber composition deeply colors the fibers. Such incorporation also increases the thermal emissivity of structures produced from them. This control of thermal emissivity is very useful in design and development of thermal control structures and systems such as heat-shielding, reflecting-retaining, or insulating curtains and curtains for heat-treating furnaces, lightweight acoustical and thermal insulation for high temperature equipment, such as heating mantles and thermal curtains, Space Shuttle tile and the like (see U.S. Pat. No. 4,148,962).

Refractory products of this invention can be employed alone, in various applications in the form in which they are obtained as fired, or their physical form can be modified, e.g., comminuted or pulverized to form a powder, or in their form as prepared or as modified they can be mixed or coated with or bonded to other materials, e.g., composite matrix materials. Cermet precursors of the invention can be coated onto inorganic substrates capable of withstanding processing temperatures necessary to produce the cermet.

Refractories of this invention have properties which make them useful in many environments.

In their porous form, refractory articles are useful in filtering or adsorption applications, for example as filters to remove solids from hot gases, as a chromatographic column packing to selectively separate or resolve liquids or gases, or as catalysts or catalyst supports.

In their fiber form, they may be exposed to high temperatures (e.g., 800° to 1400° C., preferably 1000° to 1400° C.) and maintain their integrity, i.e., they can remain strong, flexible, and continuous. Fibers can be subjected to ordinary textile processing to produce multi-filament textile structures such as rovings, cords, yarns, and the like, and can be worked into non-woven, woven, and knitted fabrics by conventional techniques. Fibers or yarns of this invention can be used together with other inorganic fabrics which can be colored in making fabrics with decorative designs. Fibers or yarns of this invention can be plied, woven, or interwoven with fibers of other materials, such as metal fibers, silica fibers, carbon, graphite, Teflon TM (E.I. duPont de Nemours) or fiberglass, and felted, knitted, and braided if desired. It may be preferable to weave precursor fibers first, then fire in a hydrogen reducing atmosphere to convert to fabric of cermet fibers. Such textiles generally will have the same properties, such as high strength, flexibility, refractoriness, and chemical and fracture resistance, as the fibers from which they are made.

Woven cloths made from the refractory fibers can be firmly bonded using refractory cements as well as colloidal silica, to form flexible cermet papers or mats useful as thermal insulation or preforms for reinforced resin composites.

Refractory cermets of this invention can also be used as reinforcement for ceramic composites, such as silica, glass, aluminum silicate, and other inorganic materials, such reinforced ceramics being in the form of blocks, paper, and other shaped articles used in high temperature environments. Spinels also have uses as high emissivity materials in thermal control and protection systems.

Another particularly useful application for the refractory products of this invention is that of reinforcement for structural polymeric, metallic, or ceramic composites, especially those composites used in high temperature environments or even hyperthermal environments found in the aerospace industry, for example in ablative applications. As composite reinforcement, refractory products of this invention are preferably used in the form of fibers (either in continuous or staple form), though other particulate forms, such as microspheres, aggregates, powders, and flakes, can be used for such purposes. Matrix materials which can be so reinforced include any of those heretofore used in making such composites, such as those disclosed in the above-cited "Modern Composite Materials" text and "Handbook of Reinforced Plastics," by S. S. Oleesky and J. G. Mohr, Reinhold Pub. Co., New York (1964). Plastics may be either of the thermosetting or thermoplastic types. Representative plastics which can be used include epoxy resins, polyester resins, acetal resins, acrylics, especially methyl methacrylate polymers, amino resins, especially urea-formaldehyde, and melamine-formaldehyde, alkyds, cellulosics, especially ethyl cellulose, cellulose acetate, and cellulose propionate, fluorocarbons, furanes, polyurethanes, phenolics, polyamides, polycarbonates, vinyl aromatics, such as styrene, polyolefins, especially polyethylene, and the like.

Cermets of this invention can also be used as abrasion resistant and/or reinforcing agents (especially as fibers or in particulate form) for elastomeric materials, such as rubber, e.g., natural rubber, styrene-butadiene rubber (SBR), acrylonitrile-butadiene rubber (NBR), and neoprene (WRT), for example where such rubbers are used in making passenger car or truck tires.

In the following examples, the viscosities recited are Brookfield viscosities measured at ambient room temperature. Weight percent solids data were obtained by drying and firing a sample of the viscous concentrate in air to about 900° to 1000° C. The calculated chemical compositions of the fibers were based on the oxide equivalents of calcined samples of the oxide precursor materials used in making up the fiberizing starting materials. The firing of green fibers and firing of refractory fibers to higher temperatures were all carried out by firing in air in an electric resistance-heated furnace.

Objects and advantages of this invention are further illustrated by the following examples, but the particular materials and amounts thereof recited in these examples, as well as other conditions and details should not be construed to unduly limit this invention. Unless otherwise stated, all percents are weight percents.

EXAMPLES

A typical procedure for preparing a graded cermet article of the invention for all of the examples is as follows: A first aqueous aluminum salt solution was obtained or prepared. Silica sols, when used, were then added. Requisite organic solutions were then added. All solutions were suitably stirred.

A second aqueous solution of a transition metal salt was prepared and used at the stated temperature. The first and second solutions were then mixed and the pH was adjusted by addition of concentrated nitric acid to obtain a resultant solution of pH about 4.5, unless otherwise stated.

This solution was pressure filtered through a Balston AA cartridge filter (Balston, Inc., Lexington, Mass.) in series with a one micrometer Millipore ™ (Millipore Corp., Bedford, Mass.) membrane filter under a gauge pressure of $6.9 \times 10^4 - 1.4 \times 10^5$ Pa (10-20 psig). The filterate was concentrated in a rotary evaporator under reduced pressure (water aspirator pressure) for several hours using an external water bath at 30°±2° C. until a viscous concentrate was obtained. Its stated viscosity was determined by a model RVT viscosimeter (Brookfield Engineering Laboratory, Inc., Stoughton, Mass.).

The resultant concentrate was extruded under nitrogen pressure at about $3.4 \times 10^5 - 1.4 \times 10^6$ Pa (50-200 psi) through a spinerette having thirty or forty holes of $7.6 \times 10^{-5}$ m (3 mil) diameter to yield fibers which were drawn down upon a take-up drum (16. cm, 6.25 inches or 64 cm, 25 inches respectively in diameter) positioned about 1-2 m (3-6 feet fiber draw length) below the spinerette at a take-up rate of about 0.5-1 m/s (100-200 ft per minute). Sufficient heating lamps, were used (usually one lamp per foot of fiber draw length) to assist in drying the fibers.

Samples of the dried fibers were cut from the bundle collected on the take-up drum and placed in a furnace and fired in air at the rates and temperatures indicated. The furnace was maintained at the sampling temperature for 5-30 min. before samples were withdrawn. These oxide fiber were then refired in a reducing atmosphere, typically 5% hydrogen and 95% either nitrogen or argon, to convert the fibers to a cermet structure. The furnace was maintained at the sampling temperature for about 30-60 minutes then cooled to room temperature before the samples were withdrawn.

Alternatively the dried but unfired ("green") fibers may be fired under reducing conditions in a partial hydrogen atmosphere as described above without an intermediate firing in air. In this way the cermet is produced directly.

TABLE I at the end of the examples summarizes the compositions of the cermets of Examples 1 to 9.

EXAMPLE 1

Preparation of a Cermet Fiber Containing Nickel, Alumina and Silica

A solution was prepared by dissolving 75.7 g of aluminum formoacetate (for preparation see Kirk-Othmer, Encyclopedia of Chemical Technology, 3d edition, Vol. 2, 202-204 (1978)) in 50 ml of deionized water at 75°-80° C. This solution was allowed to cool to 45°-50° C. and then the following were added in order: 3.5 g lactic acid (85%, commercially available from J. T. Baker Co., Phillipsburg, N.J.), 1.17 g silica sol (Nalco 1034A ™, 34% silica as an aqueous sol, Nalco Chemical Company, Chicago, Ill.) and 3.0 g N,N-dimethylformamide (commercially available from Matheson, Coleman, and Bell, Norwood, Ohio). Nickel acetate tetrahydrate 8.48 g; Matheson, Coleman and Bell, Norwood, Ohio) was dissolved in 20 ml of deionized water at 60° C., cooled to 50° C. and added to the solution above. The resulting solution was green and slightly hazy; it was pressure filtered ($6.9 \times 10^4 - 1.4 \times 10^5$ Pa, 10-20 psi) through a Balston ™ (Balston Inc., Lexington, Mass.) AA (nominal 0.3 micron) cartridge filter and then a 1.0 micron Millipore ™ (Millipore Corp., Bedford, Mass.) membrane filter in series into a 200 ml round-bottomed flask. The filtrate was concentrated in this flask in a rotary evaporator under reduced pressure (approximately $96.2-99.6 \times 10^3$ Pa, $29 \pm \frac{1}{2}$ inches of mercury) in a water bath of 29°-32° C. for about three hours until a viscous concentrate of viscosity of about 34.4 PaS (34,400 cps) as measured by a model RVT viscometer (Brookfield Engineering Lab., Inc., Stoughton, Mass.) was obtained.

This concentrate was extruded under nitrogen pressure (about $1.05 \times 10^6$ Pa, 150 psi) through a spinerette having 30 holes of $7.6 \times 10^{-5}$ m (3 mils) diameter to yield fibers which were drawn down upon a 0.61 m (24 inch) diameter take up drum positioned 1.2-2 m (4-6 feet) below the spinerette at a rate of 0.77 m/s (150 ft/minute). Heating lamps were positioned along the path of the drawn fibers to dry them.

A resultant hank of fiber was placed in a furnace, dropped over a clay support rod and fired from room temperature at 430° C. in 6 hours, and maintained at the temperature for 1.2 hours. This step completely dried the fibers and decomposed and removed most of the organic material. At this point the fibers were light green in color. The furnace temperature was increased to 750° C. over 1.8 hours, held there for 0.6 hour, then allowed to cool within the furnace. When cooled to nearly ambient temperature, the hank was removed and divided into several bundles; one bundle was refired in a furnace heated from room temperature to 720° C. in 1 hour, then to 765° C. in 0.5 hour, then to 850° C. in 1 hour and maintained at the temperature for 0.75 hour and allowed to cool to ambient temperature within the furnace. The resultant fibers were blue in color, had a sheen or shiny appearance, were soft to the touch and were fairly strong; i.e., they could be handled readily without damage and an individual filament resisted fracture when stressed along its length.

A bundle of these fibers was then fired in a controlled atmosphere furnace (dimensions of 75 cm diameter and 90 cm in length). The firing was done under a flowing atmosphere of a mixture of 5% hydrogen and 95% argon. It is important that the gas be "dry", i.e., have a dewpoint below about −20° C. or that it be passed through a catalytic drier, such as a Matheson model 850 (Matheson Gas Products, Seacaucas, N.J.) before entering the furnace. The flow rate during firing was several (1–10) cm$^3$/sec. After loading and sealing the furnace tube, it was flushed with the 5% hydrogen gas mixture for 5 minutes at about 10 times the normal flow rate (tens of cm$^3$/sec), then the flow rate was curtailed and the furnace heated from room temperature to 900° C. in 1.5 hours and maintained there for 1 hour. The fibers were allowed to cool within the furnace to about 50° C. at which point the 5% hydrogen mixture flow was ceased. The resultant fibers were black, shiny, soft, fairly strong, but weaker than before this firing process. The fibers were strongly attracted to a magnet.

SEM examination of a sample of this cermet fiber showed its surface to be covered by nodules or hemispheres of metallic nickel, typically $1-5 \times 10^{-7}$ m (0.1–0.5) micron) in diameter and spaced at a distance somewhat larger than their diameter.

This cermet fiber has a norminal composition by weight of 76% $Al_2O_3$, 4% $SiO_2$, and 20% Ni.

EXAMPLE 2

Preparation of Nickel, Alumina, Boria Cermet Fibers

A first solution was prepared from 101 g of a 7.25% aqueous solution of basic aluminum acetate (Niaproof TM, Niacet Corp., Niagara Falls, N.Y.; see U.S. Pat. No. 3,795,524, example 7) to which was added 4.6 g of lactic acid.

A second solution was prepared by dissolving 8.48 g of nickel acetate tetrahydrate in 20 ml of water at about 70° C. to which was added 1.2 g of boric acid (Fisher Scientific Co., Fairlawn, N.J.).

The first and second solutions were combined and 3 g of N,N-dimethylformamide were added and the resultant pH of the solution was about 4.5 to 5.

This solution was filtered, the filtrate was concentrated to a viscosity of 23 Pa.S (23,000 cps.), and spun through a forty hole spinerette according to the general directions given above.

A hank of the resultant fibers was fired from room temperture to 430° in 36 minutes, 430° C. to 750° C. in 54 minutes, and held at 750° C. for 18 minutes, and allowed to cool to room (ambient) temperature within the furnace.

Samples taken from the above fired hank were refired from room temperature to 850° C. in 50 minutes. The resultant fibers were olive green in color, shiny, and fairly strong.

A sample of these fibers was fired in a 5% hydrogen—95% argon atmosphere as described above. The furnace was heated from room temperature to 850° C. in about 0.5 hour and then to 950° C. and held at 950° C. for 1 hour. At this point the fibers were black, shiny, only slightly attracted to a magnet and friable, that is, the fibers broke readily upon handling.

The nominal composition of these fibers by weight was 60% $Al_2O_3$; 20% $B_2O_3$; and 20% Ni.

EXAMPLE 3

Preparation of Nickel-Iron Containing Alumina-Boria-Silica Cermet Fiber

A dilute solution of aluminum boroacetate and silica sol was prepared (see, for example, U.S. Pat. No. 3,795,524) having 8.26 weight percent oxide equivalent in the ratio of 62 parts $Al_2O_3$, 14 parts $B_2O_3$, and 24 parts $SiO_2$ corresponding to a molar ratio of 3 $Al_2O_3$ to 1 $B_2O_3$ to 2 $SiO_2$. To 84.75 g of this solution was added first a solution of 7.08 g ferric chloride hexahydrate (Matheson, Coleman, Bell) in 10 mL water and then a solution of 6.52 g nickel acetate tetrahydrate in 20 ml water at 50° C. The resulting solution was filtered and concentrated as above to a viscosity of 68 Pa.S and drawn into fibers as above.

These fibers were dried overnight in an oven at 45° C. and then placed in a tube furnace and fired in a flowing atmosphere of 5% $H_2$ and 95% Ar, as above. The furnace was heated from room temperature to 900° C. in approximately one hour. These fibers were black in color and strongly attracted to a magnet.

These fibers had a nominal composition by weight of 43% $Al_2O_3$, 10% $B_2O_3$, 17% $SiO_2$, 15% Fe, and 15% Ni.

EXAMPLE 4

Preparation of Nickel Alumina-Boria-Silica Cermet Fiber

A dilute solution of aluminum boroacetate and silica sol was prepared (see for example U.S. Pat. No. 3,795,524) having 15.45 weight percent oxide equivalent having a mole ratio of 3 $Al_2O_3$ to 1 $B_2O_3$ to 2 $SiO_2$. A solution of 48.76 g nickel acetate tetrahydrate (Fisher Scientific Co.) dissolved in 170 ml water at 80° C. was cooled to 60° C. and added to 249 g of the dilute solution above, and to this was added 10 g of concentrated nitric acid. This final solution was filtered, concentrated to a viscosity of 40 Pa.S and was drawn into green fibers as above.

A portion of these green fibers were fired in air, i.e., heated from room temperature to 430° C. in 6 hrs, held at that temperature for 1.2 hours, then heated to 750° C. in 1.7 hours and held at that temperature for 0.6 hour; the resultant oxide fibers were allowed to cool with the furnace over a period of 12 hours. These oxide fibers were re-fired in air to a temperature of 800° C. in 0.25 hour and held there for 0.75 hour.

These oxide fibers were placed in a tube furnace and fired under reducing conditions, i.e. a controlled flowing atmosphere of 5% $H_2$/95% Ar, to a temperature of 900° C., and allowed to cool with the furnace under the controlled atmosphere.

Another portion of the drawn green fibers were fired under reducing condition in a controlled atmosphere furnace using the procedure as in Example 3. Thus these fibers were converted directly to the cermet without first being converted to an oxide ceramic fiber.

Cermet fibers prepared either way had a nominal composition by weight of 48% $Al_2O_3$, 11% $B_2O_3$, 18% $SiO_2$ and 23% Ni.

SEM examination of the resulting cermet fibers showed the same morphology of sub-micron hemispherical nodules of metallic nickel on the surface of the fibers present in Example 1 above. Some differences were observed in morphology of the cermet fibers from the two processes. The fibers fired directly to the cermet were observed to have a higher density of generally smaller metallic nodules more uniform in size than those fibers which were first fired to the oxide form and then reduced to the cermet.

Magnetic measurements indicated that for those fibers first fired to an oxide form and then reduced to a cermet, in excess of 90% of the reducible metal (e.g. Ni) was present in the metallic form, whereas in the directly fired cermet fibers, nearly all (i.e. 95% or more) of the reducible metal was in the metallic phase.

In either form these cermet fibers were found to be surprisingly efficient hydrogenation catalysts capable of converting methyl oleate to methyl stearate at 270° C. and 1-dodecene to 1-dodecane at 210° C., both in the presence of hydrogen and with a surprisingly short time of contact between reactants and catalyst of less than 500 milliseconds. Such efficient hydrogenation catalysts have a variety of analytical and industrial applications.

EXAMPLE 5

Preparation of a Nickel-Cobalt-Alumina-Boria-Silica Cermet Fiber

Similar to procedures of Example 3 above, solutions of 8.46 g nickel acetate tetrahydrate in 70 ml hot water and 8.47 g cobalt acetate tetrahydrate (Malheson, Coleman, Bell) in 70 ml hot water were added consecutively to a dilute solution of 188 g of a dilute solution of aluminum boroacetate and silica sol (8.5 weight percent oxide equivalent, molar ratio $3Al_2O_3.1B_2O_3.2SiO_2$); the resulting solution had a pH of between 4.5 and 5.

The solution was filtered, concentrated, and drawn into fibers as above and fired, first in air to an intermediate temperature of 500° C. for 3 hrs and then to a maximum temperature of 850° C. and held there for 0.5 hr, then refired to 900° C. in a controlled atmosphere furnace containing 5% $H_2$ and 95% argon to a temperature of 900° C. for 1 hour, substantially as in previous examples.

The resulting cermet fibers were black, fairly strong and attracted to a magnet, and had a nominal composition by weight of 50% $Al_2O_3$, 11% $B_2O_3$, 19% $SiO_2$, 10% Ni, and 10% Co.

EXAMPLE 6

Preparation of a Lead-Alumina-Boria-Silica Cermet Fiber

In substantially the same manner as in Example 5, 1.8 g of lead acetate trihydrate (Mallinkrodt) dissolved in 5 ml of water was added to 47.7 g of a dilute solution (8.4% oxide equivalent by weight) of aluminum boroacetate and silica sol. Fibers were produced by substantially the same processes and fired in air to a maximum temperature of 750° C. and fired in a controlled atmosphere furnace containing hydrogen to a maximum temperature of 900° C.

The resulting cermet fibers were black, shiny, and brittle and had a nominal composition by weight of 50% $Al_2O_3$, 11% $B_2O_3$, 19% $SiO_2$ and 20% Pb.

EXAMPLE 7

Preparation of a Nickel-Alumina-Silica Cermet Fiber

To a solution prepared by dissolving 37.4 g of basic aluminum acetate (Niaproof TM, Niacet Corp., Niagara Falls, N.Y.) in 60 mL of hot water (75°–80° C.) was added 3.0 g of 85 percent lactic acid. A second solution was formed by dissolving 19.8 g of nickel nitrate hexahydrate in 20 mL water. This was added to 14.6 g of silica sol (31% $SiO_2$, Ludox TM LS, duPont) with vigorous stirring to prevent gelation. The resulting solution was added to the first solution above; the final solution was filtered, concentrated and drawn into fibers as described above. These fibers were fired as a bundle in air to a temperature of 750° C. over a period of 12 hours and then allowed to cool with the furnace to room temperature. Smaller hanks of the resulting oxide fibers were refired in air to temperatures of 260° C. and 900° C. for 3 hours and one hour, respectively. Portions of these hanks were fired in a controlled atmosphere furnace in an atmosphere of 5% $H_2$ and 95% Ar to a temperature of 900° C. and held there for approximately 5 minutes. Care was taken to insure that the furnace atmosphere was dry, as by passing the gas supply through a catalytic drier (e.g., Matheson 4108). (The presence of excessive amounts of water vapor can interfere with the reduction of the oxides to a cermet and can have a deleterious effect on the structural integrity and mechanical properties of the final fibers.)

Analyses of the final cermet fibers by X-ray diffraction indicated the presence of nickel metal and eta-$Al_2O_3$ in all samples. The oxide fibers exhibited the presence of $NiAl_2O_4$ in samples fired to 860° C. and above prior to the firing in the controlled atmosphere of 5% hydrogen and 95% argon. The final cermet fibers were black in color, mechanically strong and strongly attracted to a magnet. The nominal composition by weight of the cermet fibers was 58% $Al_2O_3$, 22% $SiO_2$, and 20% Ni.

EXAMPLE 8

Preparation of Nickel-Silica-Alumina-Boria Cermet Fiber

To 77.4 g of a dilute solution of aluminum boroacetate (see, for example U.S. Pat. No. 3,795,524) containing 5.91 weight % $Al_2O_3$ equivalent and 1.34 weight % $B_2O_3$ equivalent (7.25 weight % total oxide equivalent) was added the following, in order, while the solution was stirred: 7.0 g of lactic acid, 30.3 g of silica sol (34 weight % $SiO_2$, Nalco 1034 A, National Chemical Co., Chicago, Ill.), and 6.0 g of dimethylformamide. The resultant solution had a pH of approximatelly 3.5. A solution of nickel acetate tetrahydrate (16.96 g dissolved in 30 mL of water heated to approximately 55°–60° C. and cooled to about 40° C.) was then added. This final solution had a pH of about 4.5. It was filtered, concentrated and drawn into fibers as described above; the fibers were fired in air using the same firing schedule as described in Example 1 and fired in a controlled atmosphere furnace in the same manner as in Example 1. The nominal composition by weight of the cermet fibers was 23% $Al_2O_3$, 52% $SiO_2$, 5% $B_2O_3$, and 20% Ni.

The resulting cermet fibers were black, slightly dull, possessed limited mechanical strength and were strongly attracted to a magnet.

EXAMPLE 9

Preparation of a Tungsten-Alumina-Boria-Silica Cermet Fiber

A starting solution was made by adding 28 g of lactic acid and 24 g dimethylformamide to 708.6 g of a dilute aqueous solution of aluminum formoacetate (containing 7 weight % $Al_2O_3$ equivalent) (See Example 1 for method of preparing aluminum formoacetate). This solution was heated to 85° C., and 19.9 g of boric acid was dissolved directly in the heated solution. The solution was then allowed to cool to about 35° C. and then 54.9 g of silica sol (34 weight % $SiO_2$, Nalco 1034 A) was slowly added with gentle stirring. A final solution was prepared by adding a solution of 3.0 g of silicotungstic acid ($SiO_2.12WO_3.26H_2O$) dissolved in 10 mL water to 83.6 g of the solution prepared above. No pH adjustment was needed. This final solution was filtered, concentrated and drawn into fibers as described above. These drawn fibers were converted directly to cermet fibers by firing in a controlled atmosphere furnace using a dry atmosphere containing 5 weight percent hydrogen and 95 weight percent argon to a temperature between 850° C. and 900° C. over a period of 1-2 hours. The fibers were allowed to cool in the furnace under the controlled atmosphere to a temperature below 200° C. before being exposed to the air. The nominal composition of the fibers by weight was 11% $B_2O_3$, 19% $SiO_2$, 20% W, and 50% Al.

Similar cermet fibers can be fabricated in like manner by those skilled in the art having compositions containing molydenum, using molybdic acid; containing tungsten, using silico-tungstic acid; or containing copper, using copper chloride or other soluble copper salt.

TABLE I

| Ex | Components (wt %) | | | Mole ratio of oxide components | Metal(s) (wt %) |
|----|---|---|---|---|---|
| | $Al_2O_3$ | $B_2O_3$ | $SiO_2$ | | |
| 1 | 76 | 0 | 4 | 11:0:1 | Ni 20 |
| 2 | 60 | 20 | 0 | 2:1:0 | Ni 20 |
| 3 | 43 | 10 | 17 | 3:1:2 | Ni/Fe 30* |
| 4 | 48 | 11 | 18 | 3:1:2 | Ni 23 |
| 5 | 50 | 11 | 19 | 3:1:2 | Ni/Co 20* |
| 6 | 50 | 11 | 19 | 3:1:2 | Pb 20 |
| 7 | 58 | 0 | 22 | 3:0:2 | Ni 20 |
| 8 | 23 | 5 | 52 | 3:1:12 | Ni 20 |
| 9 | 50 | 11 | 19 | 3:1:2 | W 20 |

*total percent metal

Various modifications and alterations of this invention will become apparent to those skilled in the art without departing from the scope and spirit of this invention, and it should be understood that this invention is not to be unduly limited to the illustrative embodiments set forth herein.

We claim:

1. A process for making a shaped, graded cermet article comprising the steps:
   a. providing an aqueous solution containing soluble metal salts, carboxylates, and oxide sols, dispersible colloids, or mixtures thereof,
   b. concentrating said mixture to a viscous concentrate,
   c. shaping the resulting viscous concentrate into a desired formed article,
   d. gelling the formed article to provide a green non-refractory shaped article,
   e. drying and firing said green article at a temperature sufficient to convert it to a refractory ceramic article, and
   f. heating said fired article in a reducing atmosphere to provide said shaped cermet article, said article being a shaped, non-fused, cermet article comprising at least one continuous ceramic phase and containing at least one metal phase of discrete particles separated from each other, the ratio of ceramic/metal being controlled and gradually and continuously varied over the depth of the article so as to provide an article wherein the density of metal is greatest in all the exterior surface portions and decreases towards the innermost portions.

2. The process according to claim 1 wherein the firing of said green article in step e takes place in a reducing atmosphere to provide said shaped cermet article.

3. The process according to claim 1 wherein the viscous fluid of step b is sufficiently low to permit the formation of microspheres, granules, flakes, bubbles, or a coating on a substrates.

4. The process according to claim 1 further comprising heating said shaped cermet article in an oxidizing atmosphere to provide a shaped, graded, cermet/metal oxide article.

5. An article prepared according to the process of claim 1.

6. The process according to claim 1 wherein said reducing atmosphere is selected from the group consisting of hydrogen, hydrogen/argon mixture, carbon monoxide, hydrogen/helium mixture, or hydrogen mixed with any inert carrier as.

7. The process according to claim 6 wherein said reducing atmosphere is hydrogen.

8. The process according to claim 1 wherein said reducing step f takes place in the temperature range of 800° to 1000° C.

9. The process according to claim 8 wherein said reducing step f takes place in the temperature range of 800° to 900° C.

10. The article according to claim 5 which is a fiber.

11. The article according to claim 10 wherein said fiber comprises metal nodules protruding from its surface.

* * * * *

UNITED STATES PATENT AND TRADEMARK OFFICE
CERTIFICATE OF CORRECTION

PATENT NO. : 4,743,511
DATED : May 10, 1988
INVENTOR(S) : Harold G. Sowman et al.

It is certified that error appears in the above-identified patent and that said Letters Patent is hereby corrected as shown below:

Col. 6, lines 56-57, delete "deoomposes" and insert therefor -- decomposes --.

Col. 7, line 29, delete "ceadily" and insert therefor -- readily --.

Col. 13, line 36, delete "(0.1-0.5) micron)" and insert therefor -- (0.1-0.5 micron) --.

Col. 18, line 44, delete "as" and insert therefor -- gas --.

Signed and Sealed this

Twentieth Day of June, 1989

Attest:

DONALD J. QUIGG

Attesting Officer

Commissioner of Patents and Trademarks